Figure 1:
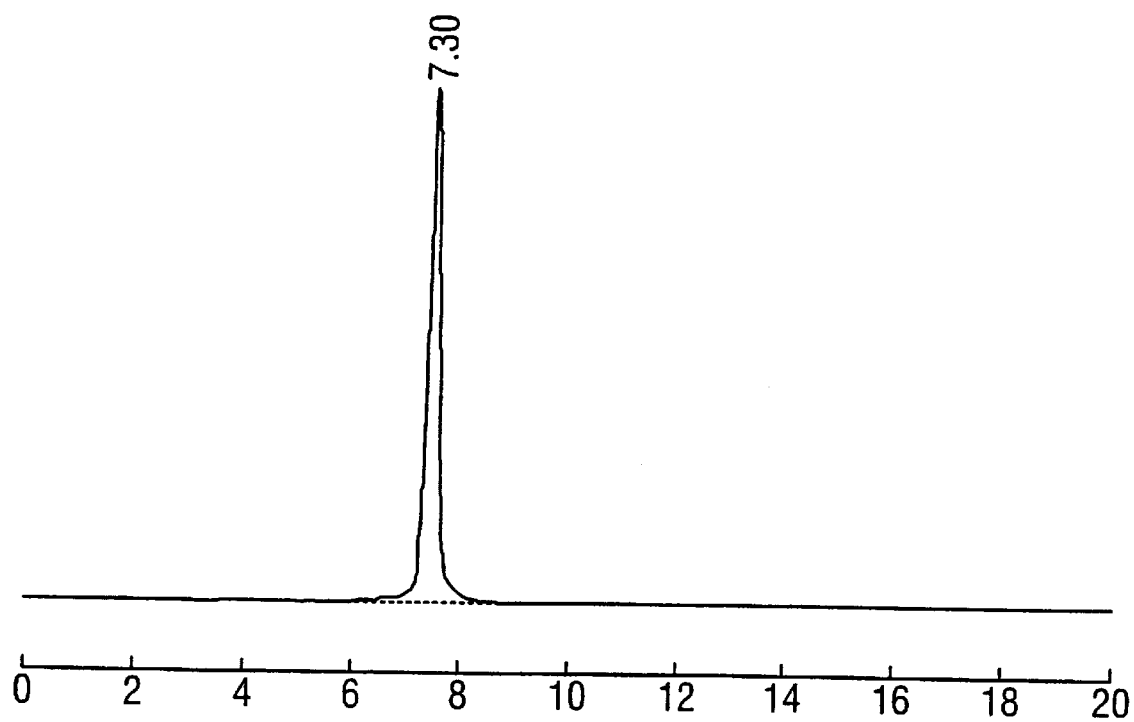

United States Patent
Ramakrishna et al.

[11] Patent Number: 6,166,070
[45] Date of Patent: Dec. 26, 2000

[54] KODAISTATINS A, B, C AND D, A PROCESS FOR THEIR PRODUCTION AND THEIR USE

[75] Inventors: Nirogi Venkata Satya Ramakrishna; Keshavapura Hosamane Sreedhara Swamy; Erra Koreswara Satya Vijayakumar, all of Mumbai; Suresh Rudra Nadkarni, Bombay; Kenia Jayvanti, Mumbai, all of India; Andreas Herling, Bad Camberg, Germany; Herbert Kogler, Glashütten, Germany; Laszlo Vertésy, Eppstein, Germany; Rajan Mukund Panshikar, Maharashtra, India; Kota Sridevi, Mumbai, India; Mythili Raman, Mumbai, India; Roda Maneck Dalal, Mumbai, India

[73] Assignee: Aventis Pharma Deutschland GmbH, Frankfurt am Main, Germany

[21] Appl. No.: 09/403,277
[22] PCT Filed: Apr. 17, 1998
[86] PCT No.: PCT/EP98/02247
  § 371 Date: Oct. 18, 1999
  § 102(e) Date: Oct. 18, 1999
[87] PCT Pub. No.: WO98/47888
  PCT Pub. Date: Oct. 29, 1998

[30] Foreign Application Priority Data

Apr. 18, 1997 [EP] European Pat. Off. ............... 97106453
Jun. 18, 1997 [EP] European Pat. Off. ............... 97109900
Nov. 24, 1997 [EP] European Pat. Off. ............... 97120536

[51] Int. Cl.[7] .................... A61K 31/34; C07D 307/32
[52] U.S. Cl. .................... 514/473; 549/313; 549/318
[58] Field of Search .................... 549/318, 313; 514/473

[56] References Cited

U.S. PATENT DOCUMENTS 5,451,573 9/1995 Hemmerle et al. .................... 514/89

FOREIGN PATENT DOCUMENTS 0 587 088 B1 3/1994 European Pat. Off. .
0 587 987 A1 3/1994 Germany .

OTHER PUBLICATIONS

Zoccoli, Michael A., "Effect of Two Inhibitors of Anion Transport on the Hydrolysis of Glucose 6–Phosphate by Rat Liver Microsomes", The Journal of Biological Chemistry, vol. 255 (3); 1113–1119 (Feb. 10, 1960).

Soodsma, James F., "The Inhibition by Phlorizin of Kidney Microsomal Inorganic Pyrophosphate–Glucose Phosphotransferase and Glucose 6–Phosphatase", The Journal of Biological Chemistry, vol. 242, (8); 1955–1960 (Apr. 25, 1967).

Wallin, Bruce K., "The Requirement For Membrane Integrity in the Inhibition of Hepatic Glucose 6–Phosphatase by Sulfhydryl Reagents and Taurocholate", Biochemical and Biophysical Research Communications, vol. 48, (3); 694–699 (Jun. 7, 1972).

Derwent Abstract XP–002061463.

*Primary Examiner*—Amelia Owens
*Attorney, Agent, or Firm*—Finnegan, Henderson, Farabow, Garrett and Dunner, L.L.P.

[57] ABSTRACT

Kodaistatins A and B, compounds of the molecular formula $C_{35}H_{34}O_{11}$, and Kodaistatins C and D, compounds of the molecular formula $C_{35}H_{34}O_{12}$, have antidiabetic activity.

7 Claims, 11 Drawing Sheets

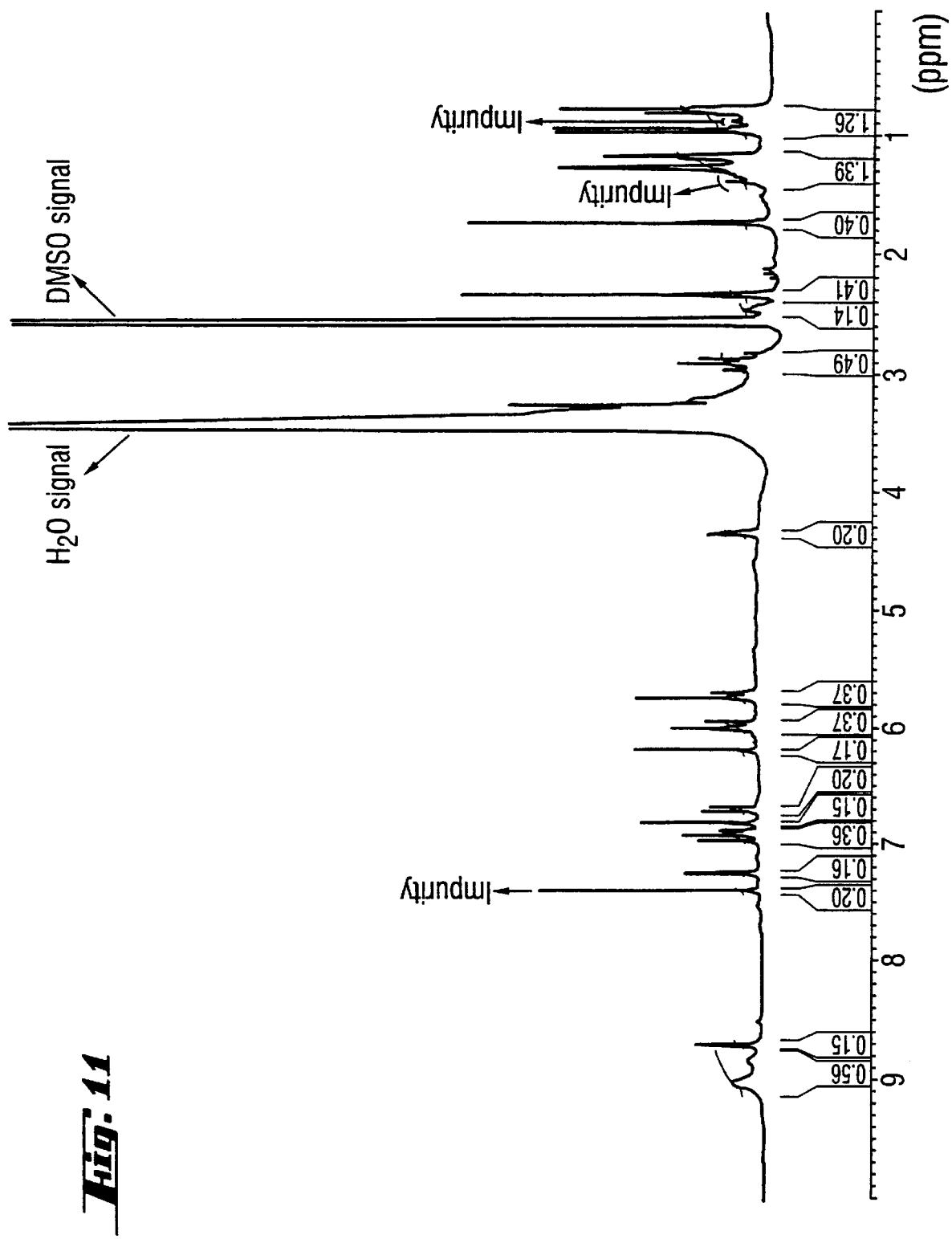

KODAISTATINS A, B, C AND D, A PROCESS FOR THEIR PRODUCTION AND THEIR USE

This invention relates to novel named Kodaistatins A, B, C and D, a process for their production and their use.

Increased rate of hepatic glucose output is a general feature of diabetes mellitus. In particular, there is a strong correlation between fasting plasma glucose level in non-insulin dependent diabetes mellitus (NIDDM) and hepatic glucose output. The two pathways by which glucose is produced in the liver are gluconeogenesis and glycogenolysis. The terminal steps of both pathways is catalysed by the microsomal glucose-6-phosphatase, a key enzyme in the homeostatic regulation of blood glucose levels. The level of this enzyme has also been known to be elevated in both experimental and pathological conditions of diabetes. Interference with this enzyme system should, therefore, result in a reduced hepatic glucose production.

Hepatic glucose-6-phosphatase is a multi component system comprised of at least three functional activities: a glucose-6-phosphate translocase (T1), a glucose-6-phosphate phosphohydrolase and a phosphate/pyrophosphate translocase (T2). The glucose-6-phosphate translocase facilitates transport of glucose-6-phosphate into the lumen of the endoplasmic reticulum (ER). The phosphohydrolase, with its active site situated on the lumenal surface of the ER, hydrolyses glucose-6-phosphate and releases glucose and phosphate into the lumen. While the efflux of phosphate is facilitated by the phosphate/pyrophosphate translocase, the exact mechanism of glucose efflux is still not clear.

The high degree of substrate specificity of glucose-6-phosphate translocase makes this a potential target for pharmacological intervention in the treatment of diabetes mellitus. Thus, amongst physiologically occurring sugar phosphates, only glucose-6-phosphate is transported by the transiocase. In contrast, the phosphatase is non-specific and is known to hydrolyse a variety of organic phosphate esters. A) A series of non-specific inhibit of giucose-6-phosphatase has been described in the literature e.g. phlorrhizin [J. Biol. Chem., 242, 1955–1960 (1967)], 5,5'-dithio-bis-2-nitrobenzoic acid [Biochem. Biophys. Res. Commun., 48, 694–699 (1972)], 2,2'-diisothiocyanatostilbene and 2-isothiocyanato-2'-acetoxystilbene [J. Biol. Chem., 255, 1113–1119 (1980)]. The first therapeutically utilizable inhibitors of the glucose-6-phosphatase system have been proposed in European Patent Publication No's. 587087 (Application No. 93 114 260.8) and 587088 (Application No. 93 114261.6).

It has now been found, that Kodaistatins A, B, C and D have an enzyme inhibitory activity, in particular with respect to glucose-6-phosphate translocase.

Accordingly, a subject of the present invention is:

1) Kodaistatin A and Kodaistatin B, compounds of the molecular formula $C_{35}H_{34}O_{11}$, and the pharmaceutically acceptable salts, esters, ethers and obvious chemical equivalents thereof.

Kodaistatin B has a hitherto unreported novel structure, formed by a o-hydroquinone, phenol, unsaturated γ-lactone, dihydroxy-cyclopentenone and α,β,γ,δ-unsaturated carbonyl moieties and is a diastereomer of Kodaistatin A.

Kodaistatins A and B are compounds of formula I below:

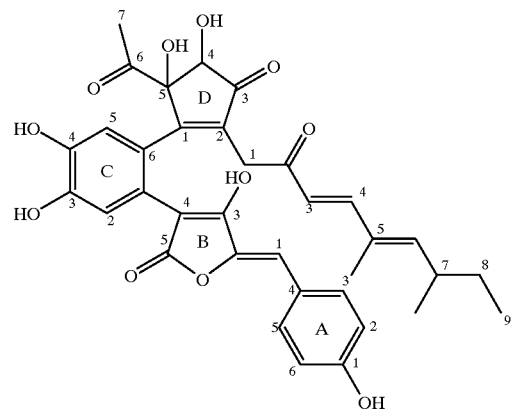

The present invention also to:

2) Kodaisatin C and Kodaisitantin D, compounds of the molecular formula $C_{35}H_{34}O_{12}$, and the pharmaceutically acceptable salts, esters, ethers and obvious chemical equivalents thereof.

Kodaistatin C has a hitherto unreported novel structure, formed by o-hydroquinones, unsaturated γ-lactone, dihydroxy-cyclopentenone and α,β,γ,δ-unsaturated carbonyl moieties. Kodaistatin D is a diastereomer of Kodaistatin C. The structural formulae of the Kodaistatins C and D differ from the structural formula I given above by the addition of an –OH group, most likely on the terminal phenyl A at position 6.

The present invention accordingly relates to all stereosomeric forms of Kodaistatin as well as to their mixtures. The single stereoisomeric forms can be isolated by known methods for example normal phase chromatography, anion-exchange chromatography, HPLC or selective crystallization.

The physiologically tolerable salts (e.g. Na, K, ammonium salts), the esters (e.g. esters with organic acids) as well as chemical equivalents (oxidation products, addition produces such as hydrates) can be produced in a manner Known to a person skilled in the art.

Another object of the crescent intention is to provide a process for the production of the novel compounds Kodaistatin A, B, C and D from culture number HIL-051652, its mutants and variants. The said process comprises cultivation of culture HIL-051652, its mutants and variants, under aerobic conditions in a nutrient medium containing sources of carbon and nitrogen, nutrient inorganic salts followed by isolation and purification of the said compound from the culture filtrate.

The nutrient medium contains sources of carbon, nitrogen inorganic salts and optionally sources of trace elements. The carbon sources may be, for example, starch, glucose, sucrose, dextrin, fructose, molasses, glycerol, lactose or galactose, preferably starch. The sources of nitrogen are, for example, soyabean meal, peanut meal, yeast extract, beef extract, peptone, tryptone, malt extract, corn steep liquor, gelatin or casamino acids, preferably tryptone and yeast extract. The nutrient inorganic salts may be, for example, sodium hydrogen phosphate, potassium hydrogen phosphate, sodium chloride, calcium chloride, calcium carbonate, potassium nitrate, ammonium sulphate or magnesium sulphate, preferably sodium chloride and calcium carbonate.

Cultivation of culture No. HIL-051652 may be carried out at temperatures between 25 and 30° C. and pH between 6.0 and 8.0. Preferably culture No. HIL-051652 is cultivated at 25° C. (±1° C.) and pH about 7.0.

The fermentation is preferably carried out for 40 to 90 hours when an optimal yield of the compounds of the present invention are obtained. It is particularly preferred to carry out the fermentation for 45–70 hours under submerged conditions for example in shake flasks as well as in laboratory fermenters. If desired, antifoam agents like Desmophen® (Polypropylene oxide, Bayer A G, Leverkusen, Germany) may be used in the fermentation process. The progress of fermentation and formation of Kodaistatins A, B, C and D can be detected by measuring the glucose-6-phosphate activity in untreated and Triton X-100® disrupted rat liver microsomes in microliter plates at room temperature using a colorimetric assay as described in Methods in Enzymology, 174,58–67 (1989) with some modification and by HPLC In the resulting culture broth, kodaistatin B, C and D are present as minor compounds, and kodaistatins A as a major compound. Thus, the active crude material can be recovered by extraction of mycelium with water miscible solvents such as methanol, ethanol and acetone, and extraction of the culture filtrate with a water immiscible solvent such as ethyl acetate, dichloromethane, chloroform or butanol at pH 5–8 or by hydrophobic interaction chromatography using polymeric resins such as "Diaion HP-20®" (Mitsubishi Chemical Industries Limited, Japan), "Amberlite XAD®" (Rohm and Haas Industries U.S.A.) activated charcoal or ion exchange chromatography at pH 5–8. The preferred method is adsorption over "Diaion HP-20®" followed by desorption of the compound using eluants such as water, methanol, acetone or acetonitrile or combinations thereof. Concentration and lyophilization of the active eluates gives the crude compound.

The crude material can be further purified by using any of the following techniques: normal phase chromatography (using alumina or silica gel as stationary phase and eluents such as ethyl acetate, chloroform, methanol or combinations thereof), reverse phase chromatography (using reverse phase silica gel like dimethyloctadecylsilylsilica gel also called RP-18 or dimethyloctylsilylsilica gel also called RP-8 as stationary phase and eluents such as water, buffers viz. phosphate, acetate, citrate (pH 2–8) and organic solvents methanol, acetonitrile or acetone. or combinations of these solvents), gel permeation chromatography using resins such as 'Sephadex LH-20®' (Pharmacla Chemical Industries, Sweden), TSKgel 'Toyopearl HW-40F®' (TosoHaas, Tosoh Corporation, Japan) in solvents such as methanol, chloroform or ethyl acetate or their combinations or "Sephadex®" G-10"and G-25 in water; or by ion exchange chromatography, preferably by anion exchange chromatography: or by counter-current chromatography using a biphasic eluent system made up of two or more solvents such as water and chloroform. These techniques may be used repeatedly or a combination of the different techniques may be used. The preferred method is chromatography over Toyopearl followed by reverse phase modified silica gel (RP-18).

The microorganism, culture number Y-93,02839 (HIL-051652), henceforth referred to as HIL-051652, used for the production of Kodaistatins A, B, C and was isolated from a soil sample collected in Kodaikanal, Tamil Nadu, India. The microorganism, HIL-051652 has been identified as *Aspergillus terreus* Thom. The microorganism was deposited on Oct. 21, 1996 with the German Collection of Microorganisms and Cell Cultures, Braunschweig, Germany with an accession number DSM No. 11247.

Kodaistatins A, B, C and D inhibit potently the activity of rat liver microsomal glucose-6-phosphate translocase. The approximate $IC_{50}$ values are given below:

| Kodaistatin A: | 0.2 μg/ml (about 300 nM) |
| Kodaistatin B: | 0.3 μg/ml |
| Kodaistatin C: | 0.09 μg/ml |
| Kodaistatin D: | 0.5 μg/ml |

In contrast, Kodaistatin A inhibits phosphatase activity in detergent-disrupted microsomes with an $IC_{50}$ of about 200 μg/ml (about 300 μM) indicating a high degree of specificity for translocase. Further, Kodaistatin A did not affect the activity of phosphate/pyrophosphate translocase. Kodaistatin A is a reversible and competitive inhibitor of glucose-6-phosphate translocase.

Kodaistatin A was further evaluated in isolated rat hepatocytes for its effect on glucose output. It inhibits both fructose-induced gluconeogenesis and glucagon-induced glycogenolysis with $IC_{50}$ values of about 25 μg/ml and 50 μg/ml respectively.

Accordingly, another object of the present application is the use of Kodaistatins A, B, C and D as pharmaceuticals and the use of Kodaistatins A, B, C and D for the production of pharmaceuticals having an anti-diabetic action. A further object of the present application is the provision of pharmaceuticals containing an active amount of kodaistatins A, B, C and D respectively.

The galenic formulation, the method of administration as well as the dosage range of the Kodaistatins depends on the species to be treated and on the state of the respective disease/disorder and can be optimized using methods known in the art. In this respect, reference is made to be citations mentioned in paragraph A) above. Kodaistatins A, B, C and D can be administered orally, intramuscularly or intravenously. They can be prepared by mixing the compounds with one or more pharmacologically tolerated auxiliaries and/or excipients such as fillers, emulsifiers, lubricants, masking flavours, colorants or buffer substances, and converted into a suitable pharmaceutical form such as tablets, coated tablets, capsules or a suspension or solution suitable for parenteral administration.

Examples of auxiliaries and/or excipients which may be mentioned are tragacanth, lactose, talc, agar-agar, polyglycols, ethanol and water. Suitable and preferred for parenteral administration are suspension or solutions in water. It is also possible to administer the active substances as such, without vehicles or diluents, in a suitable form, for example, in capsules.

The compounds may be converted into their pharmaceutically acceptable derivatives like esters and ethers. Esters may be prepared by reacting the compounds with carboxylic acids in the presence of a catalyst or by treating the compounds with acylating agents such as acid chlorides. Other methods of preparation of esters are given in the literature, for example in Advanced Organic Synthesis, 4th Edition, J. March, John Wiley & Sons, 1992.

Ethers may be prepares from the compounds by reaction with alkylating agents under basic conditions. Other methods of preparation of ethers are given in the literature, for example in Advanced Organic Synthesis, 4th Edition, J. March. John Wiley & Sons, 1992.

The following examples are illustrative of the present invention but not limitative of the scope thereof:

EXAMPLE I

Isolation of the culture HIL-051652 from soil
(a) Composition of nutrient isolation medium (Sabouraud agar)

| | |
|---|---|
| Peptone | 10.0 g |
| Glucose | 40.0 g |
| Agar | 13.0 g |
| Demineralized water | 1.0 liter |
| pH | 7.0 |

(b) Soil plating and isolation 10 g of soil collected from Kodaikanal, Tamil Nadu, India was added to 90 ml of sterilized demineralized water in 250 ml Erlenmeyer flask which was then shaken for 2 hours on a rotary shaker (220 rpm). The above soil suspension was then serially diluted in steps of 10 up to $10^{-5}$. From the last dilution, 1 ml of suspension was placed at the centre of a sterile glass petri plate (15 cms diameter) in which was then poured approximately 50 ml of the above isolation medium supplemented with 50 µg/ml of chloramphenicol and 0.5% sodium propionate. The medium was cooled to 45° C. and the plate swirled thoroughly. The mixture of soil suspension and medium was allowed to settle and incubated at 25° C. (±1° C.) for 7 days. The petri plate was periodically observed and the culture No. HIL-051652 was isolated from the growing microorganisms.

EXAMPLE II

Maintenance of the culture HIL-051652

Culture No. HIL-051652 was maintained on Sabouraud agar medium mentioned in Example I.

After dissolving the above mentioned ingredients thoroughly by heating, it was distributed in test tubes and then sterilized at 121° C. for 20 minutes. The test tubes were then cooled and allowed to solidify in a slanting position. The agar slants were streaked with the growth of the culture No. HIL-051652 by a wire loop and incubated at 25° C. (±1° C.) until a good growth was observed. The well grown cultures were stored in the refrigerator at 8° C.

EXAMPLE III

Fermentation of culture HIL-051652 in shake flasks

Composition of seed medium:

| | |
|---|---|
| Starch | 15.0 g |
| Glucose | 5.0 g |
| Soyabean meal | 15.0 g |
| Yeast extract | 2.0 g |
| Corn steep liquor | 1.0 g |
| NaCl | 5.0 g |
| CaCO$_3$ | 2.0 g |
| Demineralized water | 1.0 liter |
| pH | 6.8 |

The above seed medium was distributed in 80 ml amounts in 500 ml Erlenmeyer flasks and autoclaved at 121° C. for 20 minutes. The flasks were cooled to room temperature and each flask was then inoculated with a loopful of the above mentioned well grown culture of Example II and shaken on a rotary shaker for 72 hours at 240 rpm at 25° C. (±1° C.) to give seed culture.

Composition of the production medium

| | |
|---|---|
| Starch | 24.0 g |
| Glucose | 15.0 g |
| Tryptone | 5.0 g |
| Yeast extract | 5.0 g |
| Beef extract | 3.0 g |
| CaCO$_3$ | 4.0 g |
| Demineralized water | 1.0 liter |
| pH | 6.5 |

The production medium was distributed in 60 ml amounts in 500 ml Erlenmeyer flasks and autoclaved at 121° C. for 20 minutes. The flasks were cooled to room temperature and then inoculated with the above mentioned seed culture (1% v/v). The fermentation was carried out on a rotary shaker at 240 rpm and at a temperature of 25° C. (±1° C.) for 40–48 hours.

The production of the active compounds was monitored by measuring the inhibition of glucose-6-phosphate translocase. After harvesting, the culture broth was centrifuged and Kodaistatins A, B, C and/or D were isolated from the culture filtrate and purified as described in Example V.

EXAMPLE IV

Fermentation of the culture No. HIL-051652 in fermenters

Stage 1: Preparation of Seed Culture in Shake Flasks

The seed medium of Example III was distributed in 160 ml amounts in 1 L Erlermeyer flasks and autoclaved for 20 minutes. The seed culture was grown in these flasks as described in Example III.

Stage 2: Preparation of Seed Culture in Fermenter 75 liters of the seed medium. as described in Example III, in a 100 liters Marubishi fermenter was sterilized in situ for 45minutes at 121° C., cooled to 25°±1° C. and seeded with 3 liters of the seed culture mentioned above.

The fermentation was run with the following parameters:

| | |
|---|---|
| Temperature | 25° C. (±0.5° C.) |
| Agitation | 80 rpm |
| Aeration | 50 lpm |
| Harvest time | 50 hrs. |

Stage 3: Large Scale Fermentation 750 liters of the production medium, as described in Example III, in a 1000 liter Marubishi fermenter along with 175 ml of Desmophen® (Polypropylene oxide) as antifoam agent was sterilized in situ for 45 minutes at 121° C., cooled to 25°±1° C. and seeded with 75 liters of the seed culture from Stage 2.

The fermentation was run with the following parameters:

| | |
|---|---|
| Temperature | 25° C. (±0.5° C.) |
| Agitation | 50 rpm |
| Aeration | 350 lpm |
| Harvest time | 40–44 hrs. |

The production of the active compound was monitored by measuring the inhibition of glucose-6-phosphate translocase. When fermentation was discontinued, the pH of the culture broth was 6.0–7.0. The culture broth was centrifuged after harvesting and the glucose-6-phosphate translocase inhibitors Kodaistatins A, B, C and/or D were isolated from the culture filtrate as described below in Example V.

EXAMPLE V

Isolation and purification of Kodaistatins A, E, C and/or D:

Approximately 1000 liters of the culture broth was harvested and separated from the mycelium (110) by centrifugation. Kodaistatins A, B, C, and D were found to be present in mycelium as well as in the culture filtrate. The culture filtrate (830 liters) was combined with extract of the cell mass with 30% methanol in water (330 liters) passed through a column of Diaion HP-20® (35 liters, 3% v/v). The column was thoroughly washed with demineralized water (50 liters) and then eluted with a step gradient of $CH_3CN$ in water. Thus, the elution was done with 10% $CH_3CN$ (90 liters) and 30% $CH_3CN$ (90 liters). The fractions were collected in 15 liter measures. The active eluates (3×15 liters), obtained with 30% $CH_3CN$, were combined, concentrated under reduced pressure of 10–100 mm of Hg at 35° C. and lyophilized to yield the crude active material (225 g), Kodaistatin A showing an $IC_{50}$ of 25 µg/ml.

The crude material, thus obtained, was purified sequentially by two successive gel permeation chromatography on TSKgel Toyopearl HW-40F® varying substrate to gel ratios. Thus, the above crude material was passed separately in fifteen lots of 15 g each through Toyopearl HW-40® (1.5 liters) packed in a Latek-Saulen M 6–48 glass column. The mobile phase was 10% $CH_3CN$ in water and the flow rate was maintained at 10 ml/min at 3–5 bars. The fractions were collected in 250 ml size. The active eluates were combined, concentrated under reduced pressure of 10–100 of Hg at 35° C. and lyophilized to obtain enriched active material (3.0 g), Kodaistatin A having an $IC_{50}$ of 1–1.5 µg/ml.

The above enriched material was further fractionated in ten lots of 300 mg each by passing through TSKgel Toyopearl HW-40F® (500 ml) packed in a Latek-Saulen M 4–48 glass column. The mobile phase was 10% $CH_3CN$ in water and the flow rate was maintained at 1.5–2.0 ml/min. The fractions were collected in 20 ml measures. All the active fractions were pooled, concentrated under pressure of 10–100 mm of Hg at 35° C. and lyophilized to get semi-pure material containing the active substances, Kodaistatin A having an $IC_{50}$ of 0.375 µg/ml as the major compound and Kodaistatins B, C and/or D as the minor (0.85 g).

The Kodaistatin B, C and D were finally separated from Kodaitatin A as the mobile phase at a flow rate of 8 ml/min and detection at 294 nm to obtain pure Kodaistatin B (0.004 g), Kodaistatin C (0.011 g) and Kodaistatin D (0.004 g).

The purity of Kodaistatins B, C and D was checked by HPLC (High Pressure Liquid Chromatography) on a LiChrocart-250-4 RP Select B (5µ)column using a gradient of 0.1% aqueous orthophosphoric acid (pH 2.5) to $CH_3CN$ in 20 min at a flow rate of 1 ml/min and UV detection at 294 nm at 40° C.

The semi-pure Kodaistatin A, thus obtained, was finally purified by preparative HPLC on a 16×250 mm Eurosphere C-18 (10µ) column using 20% $CH_3CN$ in water as the mobile phase at a flow rate of 8 ml/min and detection at 294 nm to obtain pure Kodaistatin A (0.14 g) having an $IC_{50}$ of 0.2 µg/ml.

The physico-chemical and spectral properties of Kodaistatin A are summarized in Tables 1 and 1A, of Kodaistatin C in Table 2, of Kodaistatin B in Table 3 and of Kodaistatin D in Table 4.

TABLE 1

Kodaistatin A

Figure 2:
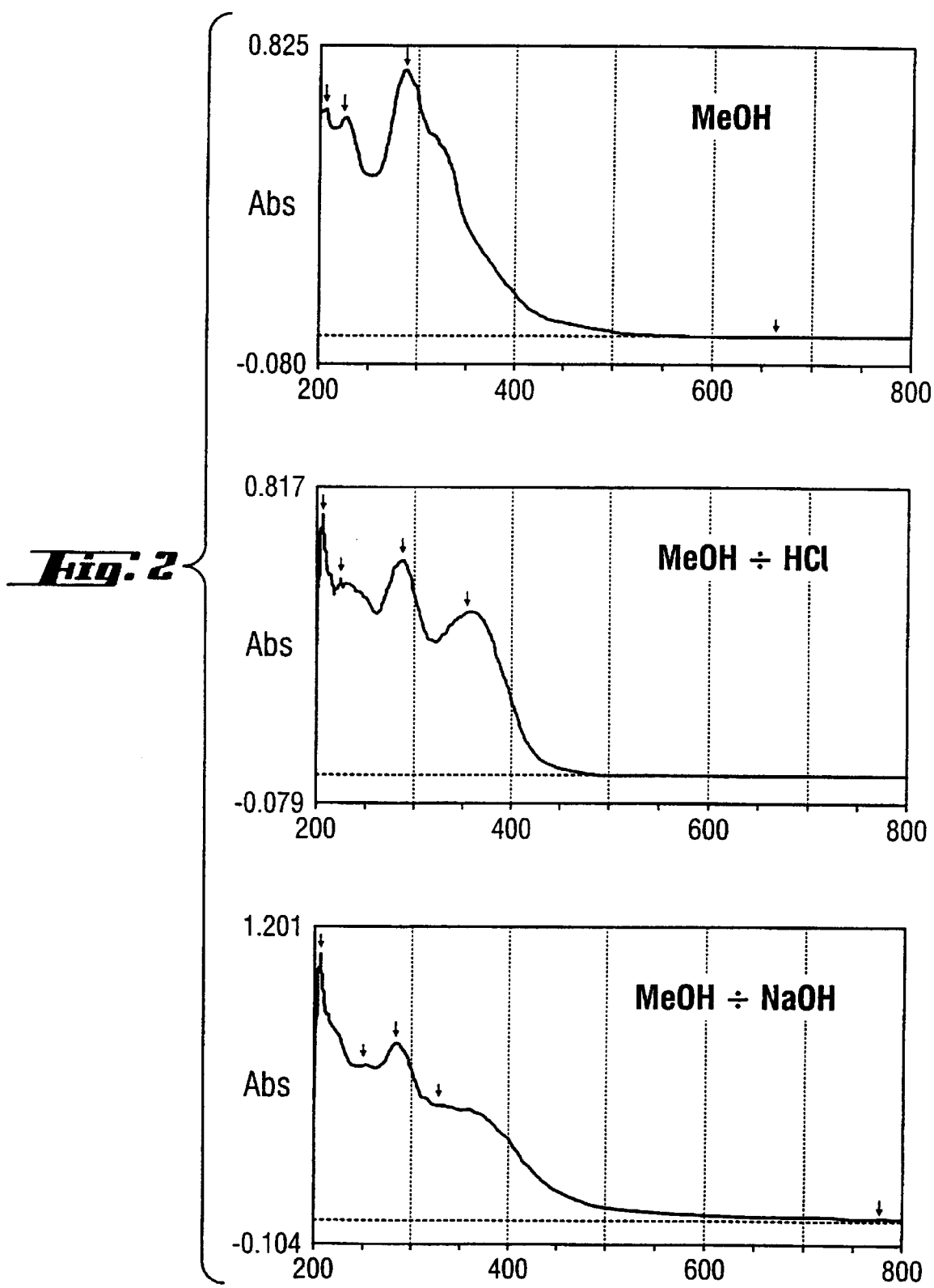
Figure 3:
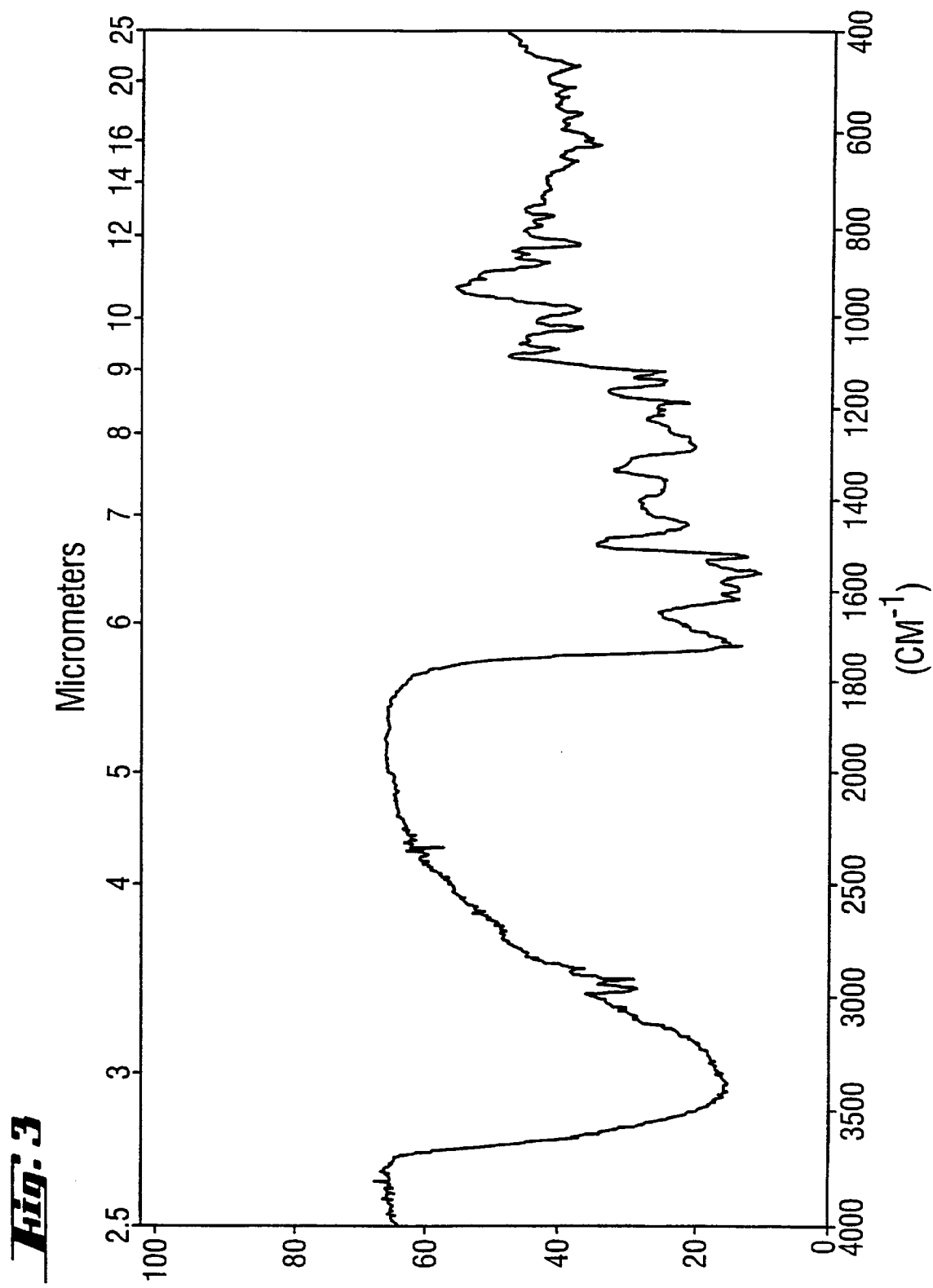
Figure 4:
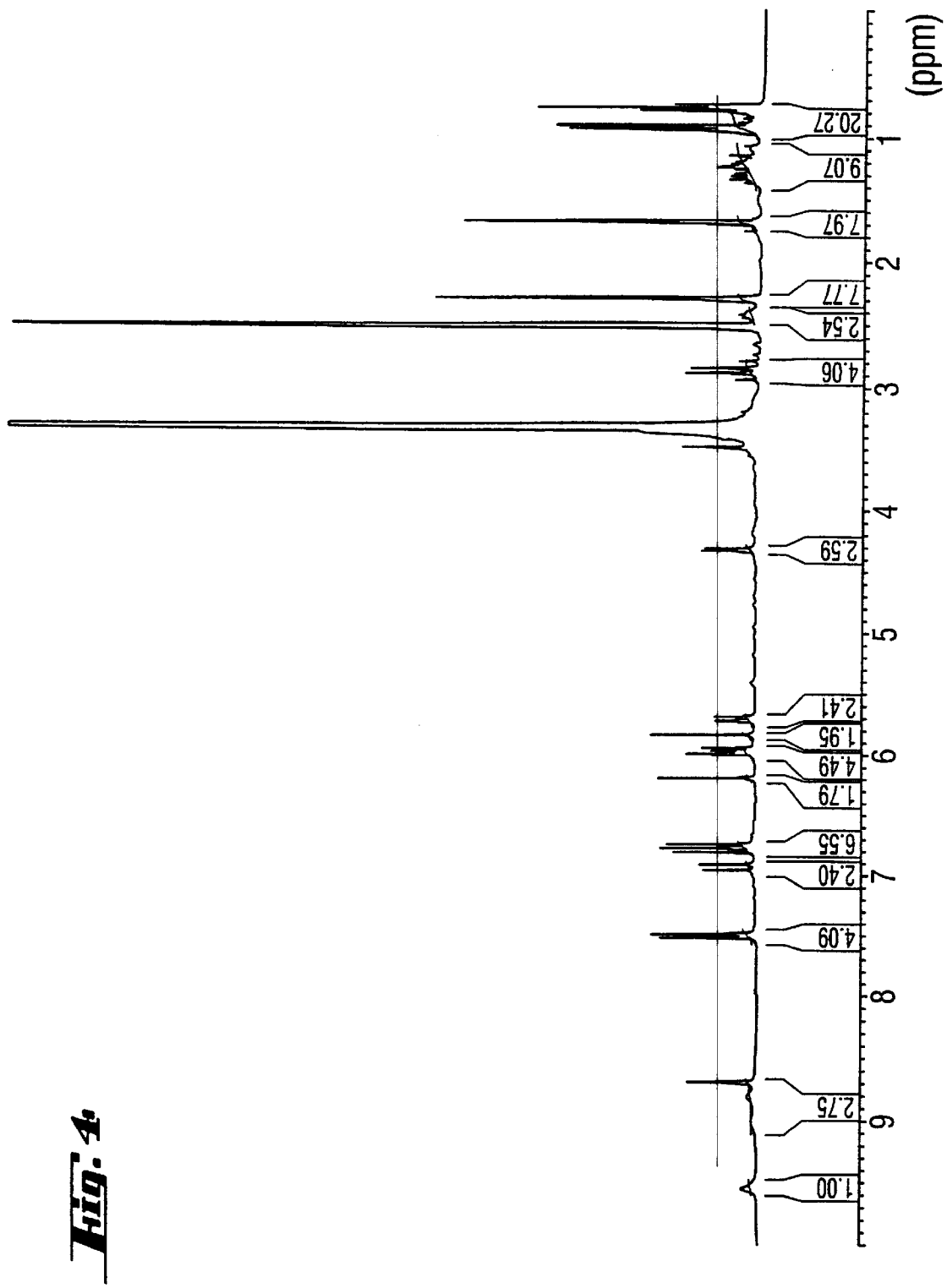
Figure 5:
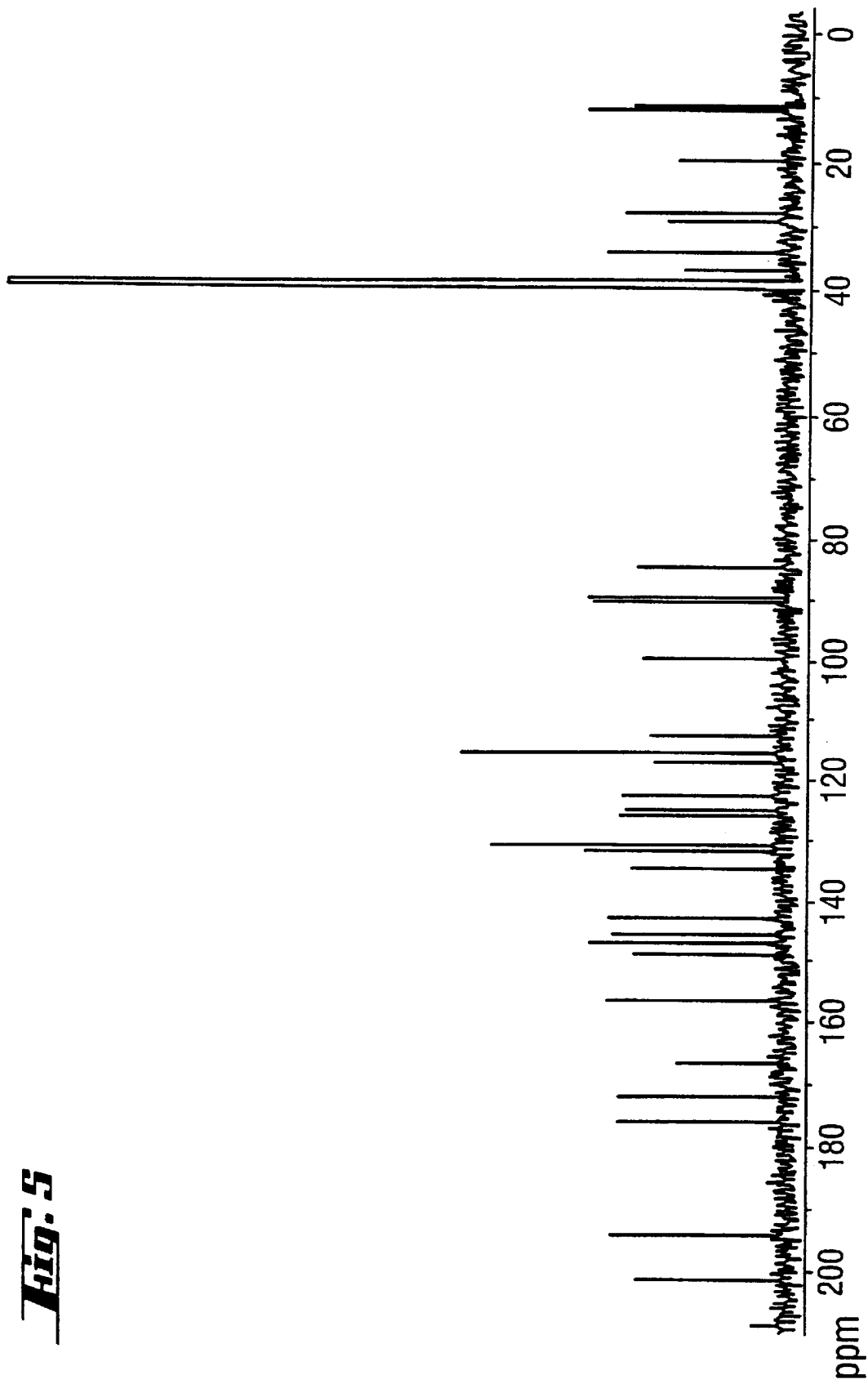

| | |
|---|---|
| Nature | Yellow solid |
| Solubility | MeOH, $CH_3CN$ and DMSO |
| Melting point | >200° C. (decomp.) |
| $[\alpha]_D$ | −85.7 ° (c 0.042, Methanol) |
| High Pressure Liquid Chromatography (HPLC) | Retention time: 7.3 min. [4 mm × (30 + 250) mm] ODS-Hypersil (5µ) column; Eluant: $CH_3CN$-$H_2O$ (20:80) Flow-rate: 1 ml/min.; Detection: 294 nm FIG. 1 of the accompanying drawings. |
| Molecular weight | 630 (ESI-MS) |
| Molecular formula | $C_{35}H_{34}O_{11}$ [Observed: m/z 631.2174 $(M + H)^+$ (HR FAB-MS, matrix: TFA/NBA, internal reference: PEG 500); Calculated for $C_{35}H_{35}O_{11}$: 631.2179] |
| UV | FIG. 2 of the accompanying drawings |
| IR (KBr) | FIG. 3 of the accompanying drawings |
| $^1$HNMR (300 MHz, DMSO-$d_6$) | FIG. 4 of the accompanying drawings |
| $^{13}$CNMR (150 MHz, DMSO-$d_6$) | FIG. 5 of the accompanying drawings |

TABLE 1A $^1$H and $^{13}$C data of Kodaistatin A in Methanol-$d_4$ ppm rei. TMS, 278K

| Position | $^1$H | $^{13}$C |
|---|---|---|
| A1 | — | 160.14 |
| A2 | 6.84 d | 116.89 |
| A3 | 7.62 d | 133.92 |
| A4 | — | 125.45 |
| B1 | 6.20 s | 110.71 |
| B2 | — | 142.01 |
| B3 | — | 166.51 |
| B4 | — | 102.86 |
| B5 | — | 172.74 |
| C1 | — | 121.65 |
| C2 | 6.87 s | 118.77 |
| C3 | — | 147.93 |
| C4 | — | 146.95 |
| C5 | 6.40 s | 114.76 |
| C6 | — | 124.24 |
| D1 | — | 163.69 |
| D2 | — | 139.12 |
| D3 | — | 202.65 |
| D4 | 4.54 s | 86.32 |
| D5 | — | 91.69 |
| D6 | — | 210.05 br |
| D7 | 2.46 s | 28.52 br |
| E1 | 3.48 d/3.23 d | 38.69 |
| E2 | — | 196.65 |
| E3 | 6.02 d | 122.94 |
| E4 | 6.96 d | 149.93 |
| E5 | — | 133.37 |
| E5-Me | 1.75 s | 12.76 |
| E6 | 5.48 d | 151.51 |
| E7 | 2.46 | 36.31 |
| E7-Me | 1.02 d | 20.85 |
| E8 | 1.34 m/1.22 m | 31.13 |
| E9 | 0.80 t | 12.51 |

TABLE 2

Figure 6:
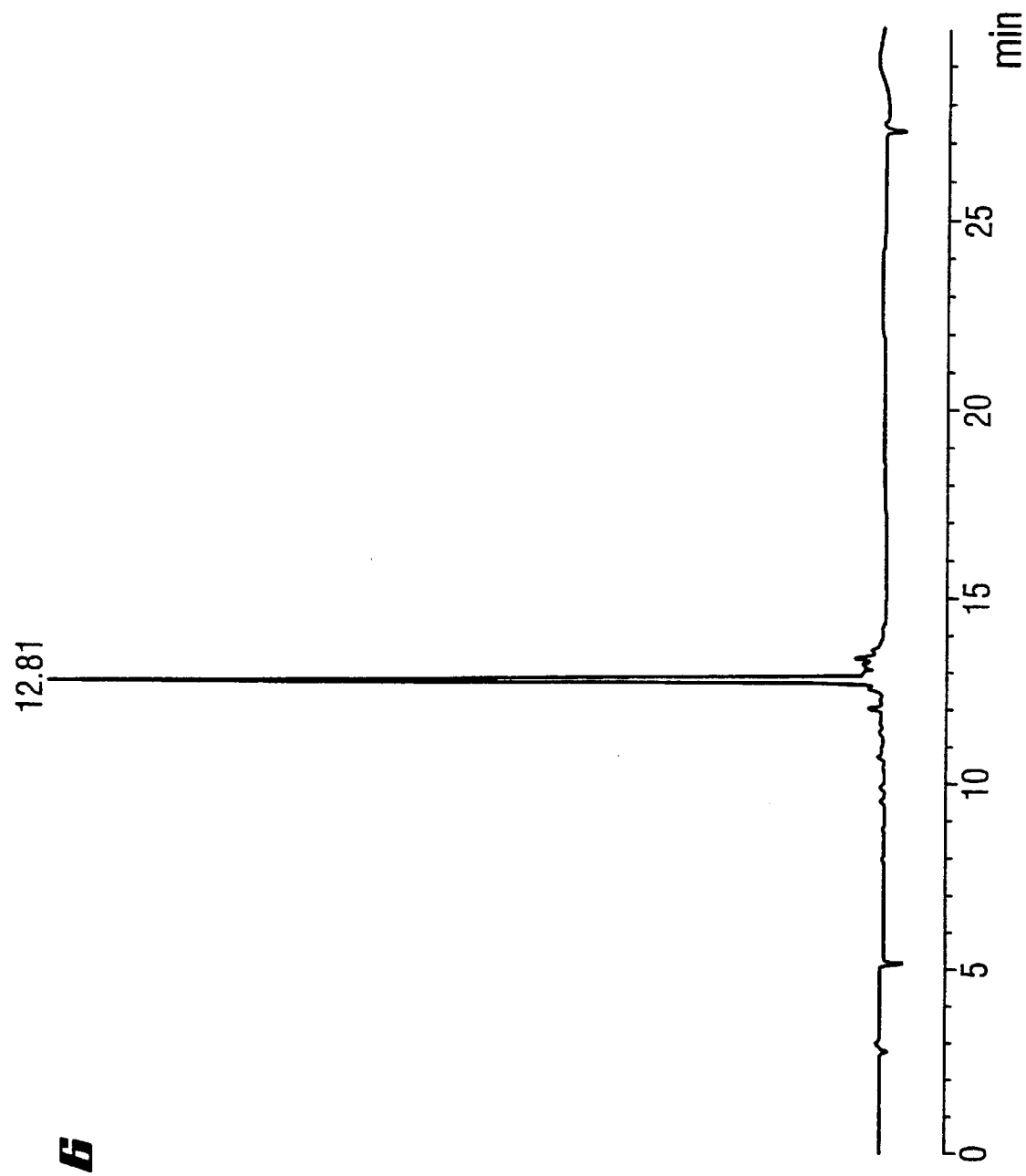
Figure 7:
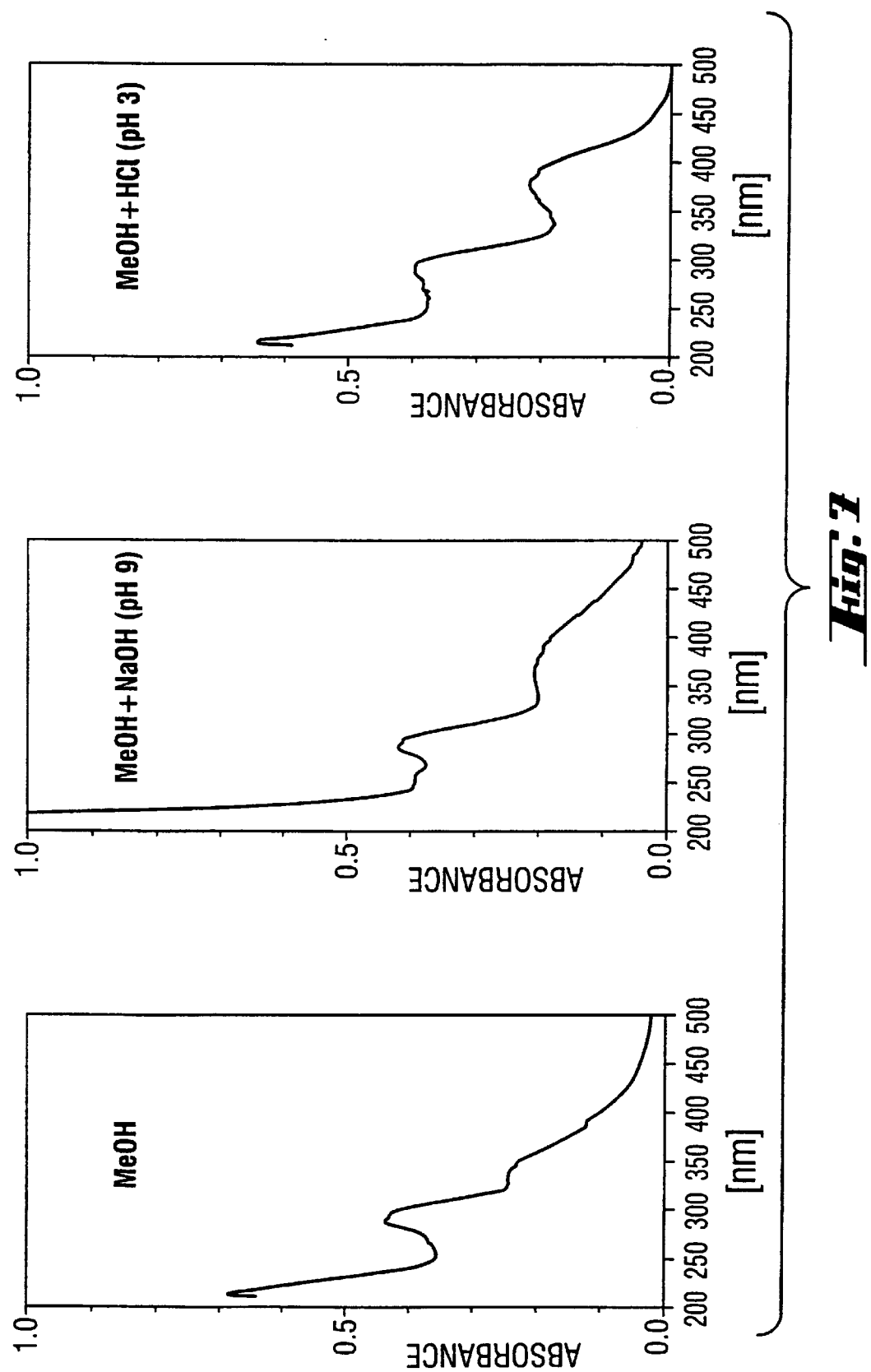
Figure 8:
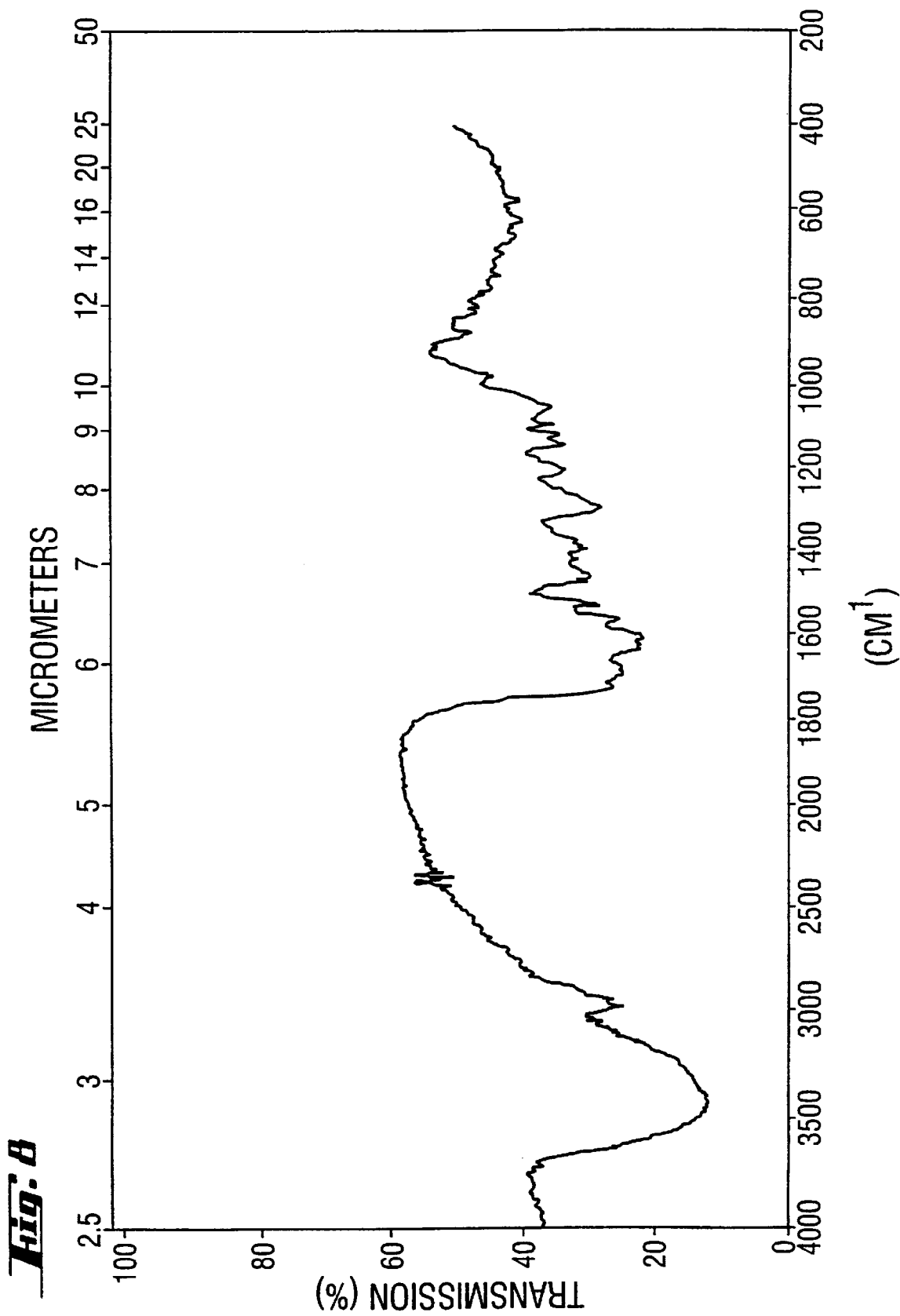
Figure 9:
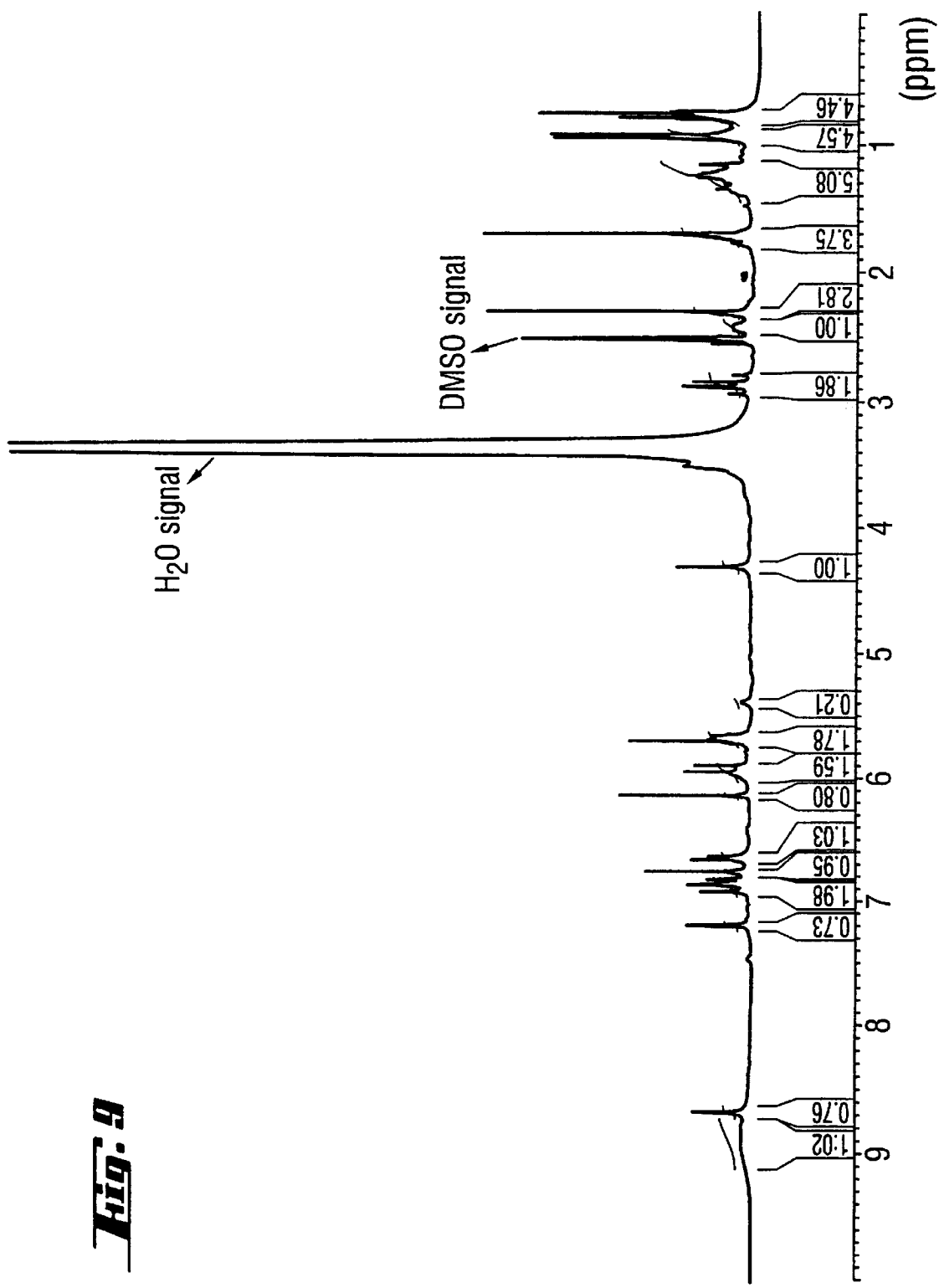

| Kodaistatin C | |
|---|---|
| Nature: | Yellow solid |
| Solubility: | MeOH and DMSO |
| Melting point: | >200° C. (decomp.) |
| $[\alpha]_D$: | −20.0° (c 0.04, Methanol) |
| HPLC RT: | 12.81 min. |
| | FIG. 6 of the accompanying drawings |
| Molecular weight: | 646 (ESI-MS) |
| Elemental analysis: | |
| Found: | C, 64.52; H, 5.41 |
| Calcd. for $C_{35}H_{34}O_{12}$: | C, 65.01; H, 5.26 |
| Molecular formula: | $C_{35}H_{34}O_{12}$ |
| UV: | FIG. 7 of the accompanying drawings |
| IR (KBr): | FIG. 8 of the accompanying drawings |
| $^1$H NMR (300 MHz,: DMSO-$d_6$) | FIG. 9 of the accompanying drawings |
| $^{13}$C NMR ($\delta$, 75: MHz, DMSO-$d_6$) | 208.78, 201.38, 194.58, 176.28, 172.24, 166.94, 148.70, 146.83, 146.61, 145.49, 145.10, 144.99, 142.76, 134.56, 131.77, 126.03, 124.86, 122.69, 122.46, 121.60, 116.99, 116.32, 115.32, 112.48, 100.12, 90.36, 89.75, 84.70, 37.29, 34.34, 29.37, 28.17, 19.95, 12.17 and 11.75 |

TABLE 3

Figure 10:
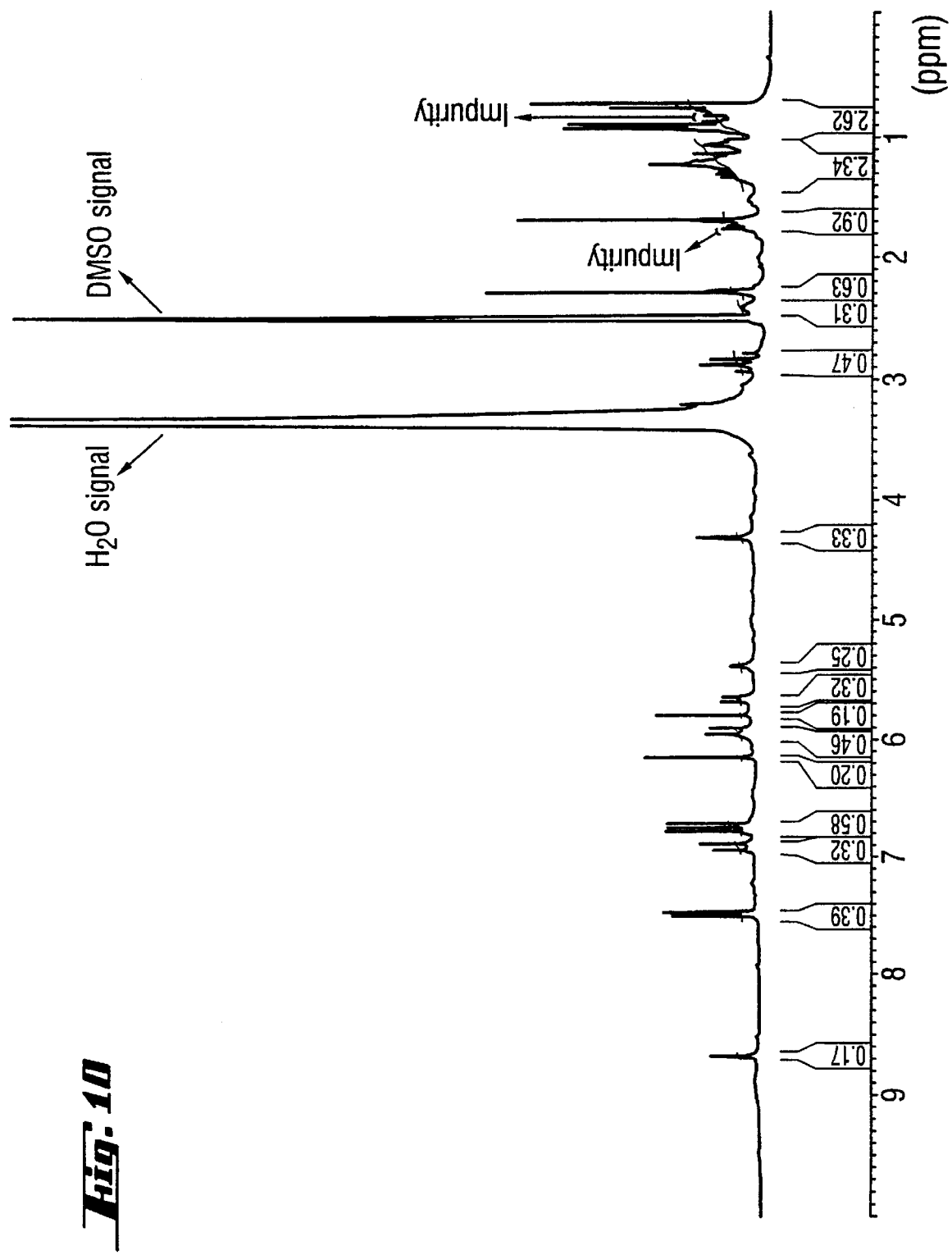

| Kodaistatin B | |
|---|---|
| Nature | Yellow solid |
| Solubility | MeOH and DMSO |
| Melting point | >200° C. (decomp.) |
| HPLC RT | 13.45 min |
| Molecular weight | 630 (ESI-MS) |
| Molecular formula | $C_{35}H_{34}O_{11}$ |
| UV (65:35 CH$_3$CN-0.1% orthophosphoric acid) | 240, 300 and 375 nm |
| $^1$H NMR (300 MHz, DMSO-$d_6$) | FIG. 10 of the accompanying drawings |

TABLE 4

| Kodaistatin D | |
|---|---|
| Nature | Yellow solid |
| Solubility | MeOH and DMSO |
| Melting point | >200° C. (decomp.) |
| HPLC RT | 12.67 min |
| Molecular weight | 646 (ESI-MS) |
| Molecular formula | $C_{35}H_{34}O_{12}$ |
| UV (65:35 CH$_3$CN-0.1% orthophosphoric acid) | 285 and 380 nm |
| $^1$H NMR (300 MHz, DMSO-$d_6$) | FIG. 11 of the accompanying drawings |

What is claimed is:

1. Kodaistatin A/B, a compound of the formula I

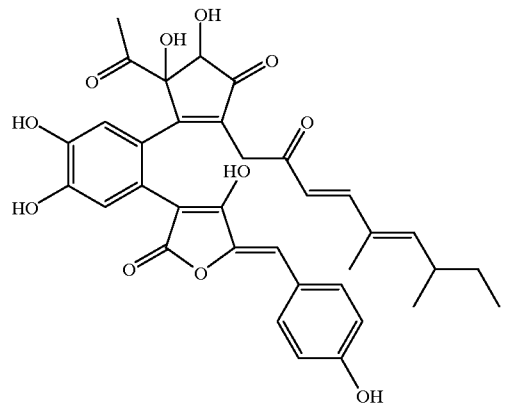

its stereoisomeric forms, and a pharmaceutically acceptable salt, ester or ethers thereof.

2. Kodaistatin A/B, a compound of the molecular formula $C_{35}H_{34}O_{11}$ and a pharmaceutically acceptable salt, ester or ether thereof.

3. Kodaistatin C/D, a compound of the formula II.

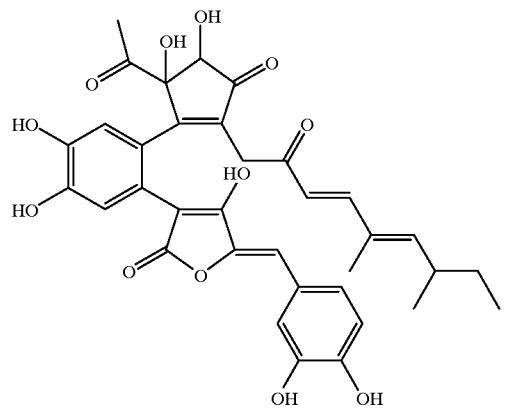

its stereoisomeric forms, and a pharmaceutically acceptable salt, ester or ether thereof.

4. Kodaistatin C/D, a compound of the molecular formula $C_{35}H_{34}O_{12}$ and a pharmaceutically acceptable salt, ester or ethers thereof.

5. A pharmaceutical comprising a compound as claimed in any one of claims 1, 2, 4 or 5 together with auxiliaries and/or excipients customary for the preparation of pharmaceuticals.

6. A method of preparing a pharmaceutical having glucose-6-phosphate translocase inhibitory activity using a compound as claimed in any one of claims 1, 2, 4 or 5.

7. A method of preparing a pharmaceutical having an anti-diabetic action using a compound as claimed in any one of claims 1, 2, 4 or 5.

* * * * *

UNITED STATES PATENT AND TRADEMARK OFFICE
CERTIFICATE OF CORRECTION

PATENT NO.    : 6,166,070
DATED         : December 26, 2000
INVENTOR(S)   : Ramakrishna et al.

It is certified that error appears in the above-identified patent and that said Letters Patent is hereby corrected as shown below:

<u>Column 10, claim 1,</u>
Line 22, "ethers" should read -- ether --.

<u>Column 10, claim 4,</u>
Line 48, "ethers" should read -- ether --.

<u>Column 10, claim 5,</u>
Line 50, "claims 1, 2, 4 or 5" should read -- claims 1, 2, 3 or 4 --.

<u>Column 10, claim 6,</u>
Line 55, "claims 1, 2, 4 or 5" should read -- claims 1, 2, 3 or 4 --.

<u>Column 10, claim 7,</u>
Line 58, "claims 1, 2, 4 or 5" should read -- claims 1, 2, 3 or 4 --.

Signed and Sealed this

Fifth Day of February, 2002

*Attest:*

JAMES E. ROGAN
*Attesting Officer*     *Director of the United States Patent and Trademark Office*